(12) United States Patent
Clapés Saborit et al.

(10) Patent No.: US 8,288,132 B2
(45) Date of Patent: Oct. 16, 2012

(54) CHEMOENZYMATIC PROCESS FOR THE PREPARATION OF IMINOCYCLITOLS

(75) Inventors: Pere Clapés Saborit, Vilassar de Dalt (ES); Jesús Joglar Tamargo, Barcelona (ES); José Antonio Castillo Expósito, Palau-Solità i Plegamans (ES); Carles Lozano Pérez, Barcelona (ES)

(73) Assignees: Consejo Superior de Investigaciones Cientificas, Madrid (ES); Bioglane, S.L.N.E., Barcelona (ES)

( * ) Notice: Subject to any disclaimer, the term of this patent is extended or adjusted under 35 U.S.C. 154(b) by 674 days.

(21) Appl. No.: 12/439,485

(22) PCT Filed: Aug. 30, 2007

(86) PCT No.: PCT/EP2007/059062
§ 371 (c)(1),
(2), (4) Date: Feb. 27, 2009

(87) PCT Pub. No.: WO2008/025826
PCT Pub. Date: Mar. 6, 2008

(65) Prior Publication Data
US 2010/0009417 A1    Jan. 14, 2010

(30) Foreign Application Priority Data
Sep. 1, 2006   (ES) .................................. 200602274

(51) Int. Cl.
*C12P 17/12*    (2006.01)
(52) U.S. Cl. ........................ 435/122; 435/121; 435/232
(58) Field of Classification Search .................. 435/121, 435/122, 232
See application file for complete search history.

(56) References Cited

U.S. PATENT DOCUMENTS

| 5,329,052 A | 7/1994 | Auger et al. |
| 2001/0018090 A1 | 8/2001 | Noda et al. |
| 2006/0222720 A1 | 10/2006 | Yamashita |

FOREIGN PATENT DOCUMENTS
WO    WO2004037001 A1    5/2004

OTHER PUBLICATIONS

Webpage from www.openthesis.org/documents/Studies-antimicrobial-activity-arginine-based-57171.html downloaded Aug. 29, 2011.*
Castillo Exposito, JA. English translation of the Submission of Doctorate Thesis request to Autonomous University of Barcelona; Barcelona, Sapin.Sep. 29, 2006, 1 page.*
Koeller, Kathryn M et al., Emerging Themes in Medicinal Glycoscience, Nature Biotechnology, Aug. 2000, pp. 835-841, vol. 18.
Kolter, Thomas et al., Chemical Chaperones—A New Concept in Drug Research, ChemBioChem, 2003, pp. 260-264, vol. 4, Wiley-VCH Verlag GmbH & Co, KGaA, Weinheim.
Asano, Naoki, Alkaloidal Sugar Mimetics: Biological Activities and Therapeutic Applications, J. Enzyme Inhibition, 2000, pp. 215-234, vol. 15.

(Continued)

*Primary Examiner* — Susan Hanley
(74) *Attorney, Agent, or Firm* — Peter B. Scull; Hamilton, DeSancts & Cha LLP

(57) ABSTRACT

The present invention discloses a chemoenzymatic process for the preparation of an iminocyclitol corresponding to formula (I), (II), (III) or (IV), wherein: $R^1$ and $R^2$ are the same or different, and independently selected from the group consisting of: H, OH, hydroxymethyl, methyl, ethyl, butyl, pentyl, hexyl, octyl, isopropyl, isobutyl, 2-methylbutyl, and benzyl; $R^3$ is selected from the group consisting of: H, hydroxymethyl, hydroxyethyl, ethyl, butyl, pentyl, hexyl, octyl, dodecyl, isobutyl, isopropyl, isopentyl, 2-methylbutyl, benzyl, and phenylethyl; n: 0 or 1; the process comprising: (i) an aldol addition catalyzed by a D-fructose-6-phosphate aldolase enzyme (FSA) and an acceptor aminoaldehyde; and (ii) an intramolecular reductive amination of the addition adduct obtained in step (i) with $H_2$, in the presence of a metallic catalyst, optionally being carried out said step (ii) in the presence of an aldehyde of formula $R^3$—CHO, wherein $R^3$ is as defined above.

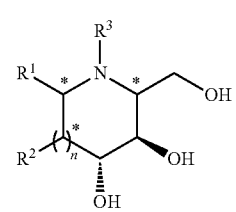

I

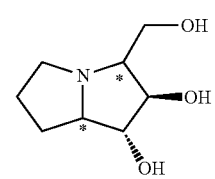

II

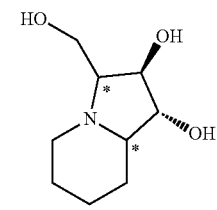

III

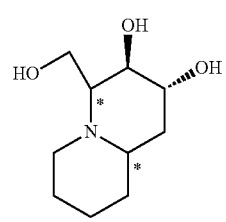

IV

8 Claims, 2 Drawing Sheets

OTHER PUBLICATIONS

Asano, Naoki, Glycosidase Inhibitors: Update and Perspectives on Practical Use, Glycobiology, 2003, pp. 93R-104R, vol. 13 No. 10, Oxford University Press.

Fiaux, H et al., Functionalized Pyrrolidines Inhibit α-Mannosidase Activity and Growth of Human Glioblastma and Melanoma Cells, J. Med. Chem, 2005, pp. 4237-4246, vol. 48, American Chemical Society.

Lillelund, Vinni H et al., Recent Developments of Transition-State Analogue Glycosidase Inhibitors of Non-Natural Product Origin, Chem. Rev, 2002, pp. 515-554, vol. 102, American Chemical Society.

Compain, Philippe et al., Design, Synthesis and Biological Evaluation of Iminosugar-Based Glycosyltransferase Inhibitors, Current Topics in Medicinal Chemistry, 2003, pp. 541-560, vol. 3, Bentham Science Publishers Ltd.

Mehta, Goverdhan et al., A Norbornyl Route to Some Novel Seven-Membered Iminocyclitols, Tetrahedron Letters, 2002, pp. 331-334, vol. 43, Elsevier Science Ltd.

Moris-Varas, Francisco et al., Enzymatic/Chemical Synthesis and Biological Evaluation of Seven-Membered Iminocyclitols, J. Am. Chem. Soc, 1996, pp. 7647-7652, vol. 118, No. 33, American Chemical Society.

Fuentes, Jose et al., Efficient Synthesis of Seven-Membered Iminocyclitols from Glycosylenamines, Tetrahedron Letters, 1999, pp. 4063-4066, vol. 40, Elsevier Science Ltd.

Li, Hongqing et al., The First Synthesis of Substituted Azepanes Mimicking Monosaccharides: A New Class of Potent Glycosidase Inhibitors, Org. Biomol. Chem, 2004, pp. 1492-1499, vol. 2, The Royal Society of Chemistry.

Lin, Chang-Ching et al., Versatile Approach for the Synthesis of Novel Seven-Membered Iminocyclitols via Ring-Closing Metathesis Dihydroxylation Reaction, Bioorg. Med. Chem, 2004, pp. 3259-3267, vol. 12, © Elsevier Ltd.

Godin, Guillaume et al., Synthesis and Biological Evaluation of the First Example of an Eight-Membered Iminoalditol, Tetrahedron Letters, 2004, pp. 579-581, vol. 45, © Elsevier Ltd.

Beutler, Ernest and Cox, Timothy M., Miglustat, Drugs 2003, pp. 2435-2436.

Von Der Osten, Claus H et al., Use of a Recombinant Bacterial Fructose-1, 6-Diphosphate Aldolase in Aldol Reactions: Preparative Syntheses of 1-Deoxynojirimycin, 1-Deoxymannojirimycin, 1,4-Dideoxy-1, 4-Imino-D-Arabinitol, and Fagomine, J. Am. Chem. Soc, 1989, pp. 3924-3927, vol. 111, American Chemical Society.

Romero, Alex et al., Chemo-Enzymatic Total Synthesis of 3-Epiaustraline, Australine, and 7-Epialexine, J. Org. Chem, 2000, pp. 8264-8268, vol. 65, No. 24, American Chemical Society.

Look, Gary C et al., Enzyme-Catalyzed Organic Synthesis: Practical Routes to Aza Sugars and Their Analogs for Use as Glycoprocessing Inhibitors, Acc. Chem. Res, 1993, pp. 182-190, vol. 26, No. 4, American Chemical Society.

Machajewski, Timothy D. et al., The Catalytic Asymmetric Aldol Reaction, Angew. Chem. Int. Ed., 2000, pp. 1352-1374, vol. 39, Wiley-VCH Verlag GmbH & Co, KGaA, Weinheim.

Jung, Sang-Hun et al., An Efficient Multigram-Scale Preparation of Dihydroxyacetone Phosphate, J. Org. Chem, 1994, pp. 7182-7184, vol. 59, No. 23, American Chemical Society.

Fessner, Wolf D. et al., Synthesis of Dihydroxyacetone Phosphate (and Isosteric Analogues) by Enzymatic Oxidation; Sugars from Glycerol, Angew. Chem. Int. Ed. Engl., 1994, pp. 209-212, vol. 33, No. 2), VCH Verlagsgesellschaft mbH.

Charmantray, Franck et al., Improved Straightforward Chemical Synthesis of Dihydroxyacetone Phosphate Through Enzymatic Desymmetrization of 2,2-Dimethoxypropane-1,3-diol, J. Org. Chem, 2004, pp. 9310-9312, vol. 69, No. 26, American Chemical Society.

Sanchez-Moreno, Israel et al., Multienzyme System for Dihydroxyacetone Phosphate-Dependent Aldolase Catalyzed C—C Bond Formation From Dihydroxyacetone, Chem. Commun, 2004, pp. 1634-1635, The Royal Society of Chemistry.

Schurmann, Melanie et al., Fructose-6-phosphate Aldolase is a Novel Class I Aldolase from *Escherichia coli* and is Related to a Novel Group of Bacterial Transaldolases, J. Biol. Chem, 2001, pp. 11055-11061, vol. 276, No. 14, The American Society for Biochemistry and Molecular Biology, Inc.

Casadaban, Malcolm J, Transposition and Fusion of the Iac Genes to Selected Promoters in *Esherichia coli* Using Bacteriophage Lambda and Mu, J. Mol. Biol, 1976, pp. 541-555, vol. 104.

Espelt, Laia et al., Stereoselective Aldol Additions Catalyzed by Dihydroxyacetone Phosphate-Dependent Aldolases in Emulsion Systems: Preparation and Structural Characterization of Linear and Cyclic Iminopolyols from Aminoaldehydes, Chem. Eur. J, 2003, pp. 4887-4899, vol. 9, Wiley-VCH Verlag GmbH & Co, KGaA, Weinheim.

Ocejo, Marta et al., A Direct and Efficient Stereoconservative Procedure for the Selective Oxidation of N-Protected β-Amino Alcohols, Synlett, 2005, pp. 0001-0003, vol. x, Georg Thieme Verlag Stuttgart.

Thorell, Stina et al., Crystal Structure of Decameric Fructose-6-Phosphate Aldolase from *Escherichia coli* Reveals Inter-subunit Helix Swapping as a Structural Basis for Assembly Differences in the Transaldolase Family, J.Mol. Biol, 2002, pp. 161-171, vol. 319, 2002 Elsevier Science Ltd.

Schurmann, Martin et al., Fructose-6-phosphate Aldolase and 1-deoxy-D-xylulose 5-phosphate Synthase from *Escherichia coli* as Tools in Enzymatic Synthesis of 1-deoxysugars, J. Mol. Catal. B-Enzym, 2002, pp. 247-252, vol. 19-20, Elsevier Science B.V.

De Luca, Lidia et al., A very Mild and Chemoselective Oxidation of Alcohols to Carbonyl Compounds, Org. Lett, 2001, pp. 3041-3043, vol. 3, No. 19, American Chemical Society.

Castillo Exposito, Jose Antonio, Studies on Antimicrobial Activity of Arginine-Based Surfactants and Chemo-Enzymatic Synthesis of Novel Amphiphilles Based on L-Arginine and D-Fagomine, Thesis 2006, p. 35-39 and 138-143 published Feb. 2, 2007.

Castillo, Jose A. et al., Fructose-6-phosphate Aldolase in Organic Synthesis: Preparation of D-Fagomine, N-Alkylated Derivatives and Preliminary Biological Assays, Org. Let., 2006, pp. 6067-6070, vol. 8, No. 26, 2006 American Chemical Society.

Sugiyama et al, D-Fructose-6-phosphate Aldolase-Catalyzed One-Pot Synthesis of Iminocyclitols, J. Am. Chem. Soc, 2007, pp. 14811-14817, vol. 29, American Chemical Society, vol. publication date Nov. 28, 2007, web publication date: Nov. 7, 2007.

Notification of Transmittal of the International Search Report and the Written Opinion of the International Searching Authority, or the Declaration, Dec. 19, 2007, European Patent Office.

GenBank Accesion No. BAA13352, MipB [*Escherichia coli*], version: BAA13552.1, Feb. 7, 1999.

Izquierdo, "Polyhydroxylated Pyrrolizidines. Part 3: A New and Short Enantiospecific Synthesis of (+) Hyacinthacine A2", Science Direct, Sep. 22, 2003, 3933-3935, University of Granada, Spain. (Annex 1).

Wikipedia Encyclopedia, "Enzyme", Definition and Etymology of the word Enzyme. Wikipedia, the Free Encyclopedia: http://en.wikipedia.org/wiki/Enzyme, Dec. 14, 2011. (Annex 2).

English translation of the Spanish priority patent application No. P 200602274 filed on Sep. 1, 2006, Spain Annex 3).

Castillo, Deposit Receipt of the Thesis at the Universitat Autonoma de Barcelona. Deposited: Sep. 26, 2006. (Annex 4), pto translation provided.

* cited by examiner

CHEMOENZYMATIC PROCESS FOR THE PREPARATION OF IMINOCYCLITOLS

FIELD OF THE INVENTION

The present invention relates to a chemoenzymatic process for the preparation of iminocyclitols. The synthesized products can be used as dietary supplements and functional ingredients for the food industry, as well as therapeutic agents (e.g. in the treatment of diabetes).

BACKGROUND ART

Polyhydroxylated compounds, such as oligosaccharides, complex carbohydrates and lipid and protein conjugates thereof, are molecules of great importance in biochemical processes of biological recognition such as cell adhesion, viral infections, cell differentiation in organ development and metastasis (Koeller, K. M., Wong, C. H., Nat. *Biotechnol.* 18 (2000) 835). Thus, the enzymes involved in their synthesis or degradation, glycosyltransferases and glycosidases respectively, constitute inhibition or activation targets (according to Kolter, T., Wendeler, M., *Chembiochem* 4 (2003) 260) since they are involved in metabolic disorders and diseases, such as type II diabetes, hepatitis B and C, Gaucher's disease, Fabry's disease, cystic fibrosis, colon cancer, or viral infections including HIV (Asano, N., *J. Enzyme Inhib.* 15 (2000) 215; Asano, N., *Glycobiology* 13 (2003) 93R; Fiaux, H., Popowycz, F., Favre, S., Schutz, C., Vogel, P., Gerber-Lemaire, S., Juillerat-Jeanneret, L., *J. Med. Chem.* 48 (2005) 4237).

Among the polyhydroxylated compounds which are inhibitors of glycosyltransferases and glycosidases, the types of iminocyclitols which stand out are pyrrolidines, piperidines, indolizidines, pyrrolizidines, nortropanes, and seven-membered polyhydroxylated iminocyclitols), among others, some of them being powerful inhibitors of glycosidases and glycosyltransferases. (Asano, N., *J. Enzyme Inhib.* 15 (2000) 215; Asano, N., *Glycobiology* 13 (2003) 93R; Lillelunh, V. H., Jensen, H. H., Liang, X., Bols, M., *Chem. Rev.* 102 (2002) 515; Compain, P., Martin, O. R., *Curr. Top. Med. Chem.* 3 (2003) 541; Mehta, G., Lakshminath, S., *Tetrahedron Lett.* 43 (2002) 331; Moris-Varas, F., Qian, X. -H., Wong, C. -H., *J. Am. Chem. Soc.* 118 10 (1996) 7647; Fuentes, J., Olano, D., Pradera, M. A., *Tetrahedron Lett.* 40 (1999) 4063; Li, H. Q., Bleriot, Y., Chantereau, C., Mallet, J. M., Sollogoub, M., Zhang, Y. M., Rodriguez-Garcia, E., Vogel, P., Jimenez-Barbero, J., Sinay, P., *Org. Biomol. Chem.* 2 (2004) 1492; Lin, C. C., Pan, Y. S., Patkar, L. N., Lin, H. M., Tzou, D. L. M., Subramanian, T., *Bioorg. Med. Chem.* 12 (2004) 3259; Godin, G., Garnier, E., Compain, P., Martin, O. R., Ikeda, K., Asano, N., *Tetrahedron Lett.* 45 (2004) 579).

Some derivatives such as miglitol and miglustat are drugs marketed for the treatment of type II diabetes (Platt, F. M., Butters, T. D., *Drugs* 63 (2003) 2435).

Some natural iminociclytols or plant extracts containing them have also been described as functional ingredients in the food industry or as dietary supplements. Thus, US20010018090 discloses the use of 1-deoxynojirimicin or an analogue thereof as a calorie reducing agent that may be incorporated in food or beverage; US20060222720 discloses an anorectic agent containing aqueous solvent extracts of Vernonia cinerea and mulberry as active ingredients; WO2004037001 discloses the addition of mulberry extracts to a sacharide containing food for regulating blood sugar levels.

So far, the chemoenzymatic strategies for the synthesis of iminocyclitols disclosed are based on the use of aldolases, enzymes capable of catalyzing stereoselective aldol condensation reactions between aldehydes and ketones. (Von der Osten, C. H., Sinskey, A. J., Barbas, C. F., III, Pederson, R. L., Wang, Y. F., Wong, C. H., *J. Am. Chem. Soc.* 111 (1989) 3924, Romero, A., Wong, C. H., *J. Org. Chem.* 65 (2000) 8264, Look, G. C., Fotsch, C. H., Wong, C. H., *Acc. Chem. Res.* 26 (1993) 182, Machajewskif, T. D., Wong, C. H., *Angew. Chem. Int. Ed.* 39 (2000) 1353; patent (US005329052A)). Among known aldolases, the dihydroxyacetonephosphate (DHAP)-dependent aldolases have focused the attention due to four reasons:

1) their availability, either because some of them are commercially available or because their preparation is relatively easy from modified *E. coli,*
2) their high stereoselectivity,
3) their wide structural tolerance for the acceptor aldehyde, and
4) their stereogenic ability.

Figure 1:
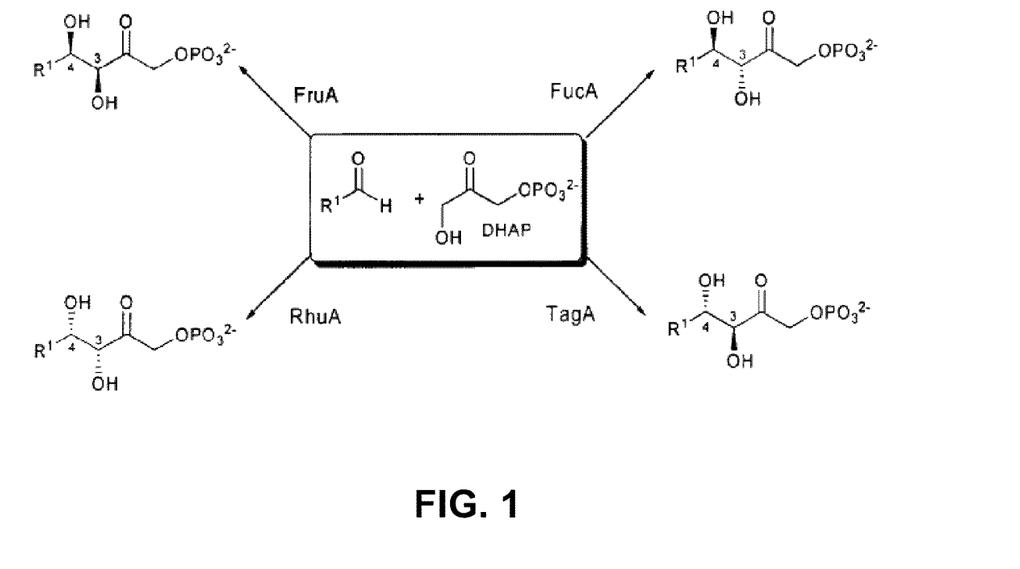
FIG. 1. Stereochemistry of DHAP-aldolases.

DHAP-dependent aldolases (DHAP-aldolases) catalyze reversible DHAP aldol addition with an acceptor aldehyde, obtaining $\alpha,\beta$-dihydroxyketones with two new stereogenic centres. It is especially interesting to note that the four stereocomplementary DHAP-aldolases (FIG. 1) are already known: D-fructose-1,6-diphosphate aldolase (FruA); L-rhamnulose-1-phosphate aldolase (RhuA); L-fuculose-1-phosphate aldolase (FucA); and D-tagatose-1,6-diphosphate aldolase (TagA). Advantageously, these biocatalysts have some ability to control the aldol addition stereochemistry, the configuration of the new generated stereogenic centres depending on the enzyme and not on the reagents.

Figure 2:
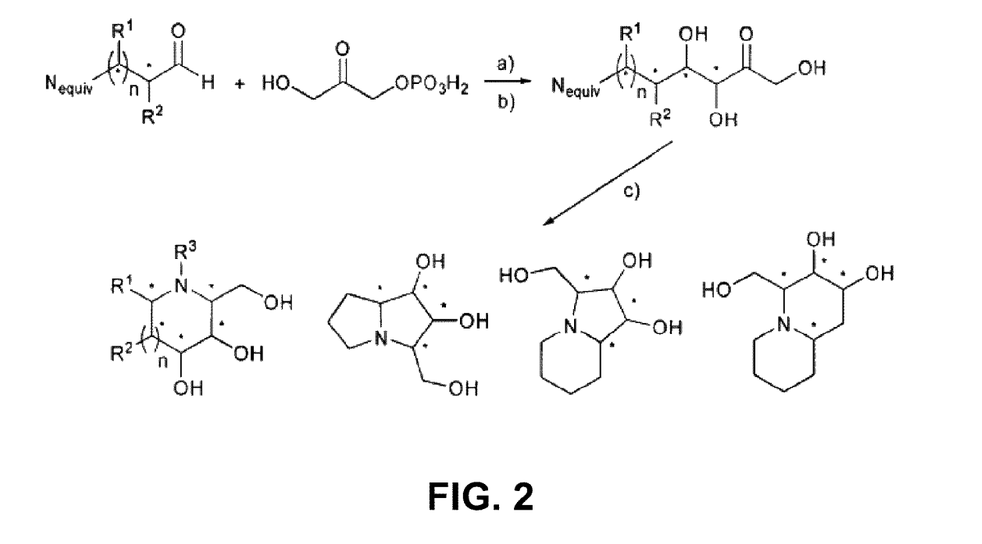
FIG. 2. General scheme of the chemoenzymatic synthesis of iminocyclitols. Nequiv: protected amine or azide, such as benzyloxycarbonyl-NH—, tert-butyloxycarbonyl-NH—, 9-fluorenylmethoxycarbonyl-NH—, phenylacetyl-NH—, and azido. a) DHAP-aldolase, b) acid phosphatase; c) intramolecular reductive amination with H$_2$ in the presence of a metallic catalyst or a reductive agent.

The general chemoenzymatic synthetic scheme of iminocyclitols synthesis using DHAP-aldolases is shown in FIG. 2. The critical step of this scheme is the aldol addition of DHAP to aminoaldehydes or synthetic equivalents thereof catalyzed by DHAP-aldolases. In this step two stereogenic centres, whose configuration depends on the enzyme, are generated, although there are numerous examples wherein, depending on the substrate, the enzyme looses selectivity, obtaining diastereomeric products. The following step is a hydrolysis of the phosphate moiety of the aldol adduct by an acid phosphatase. Finally, the Cbz removal and the transformation to iminocyclitol is generally carried out in one step.

Figure 3:
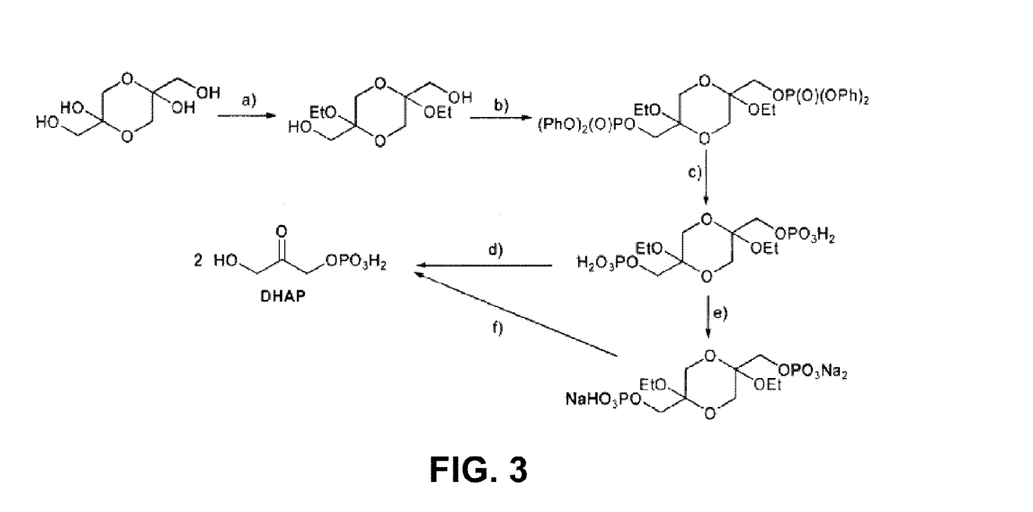
FIG. 3. Synthesis scheme of dihydroxyacetone phosphate (DHAP). a) HC(OEt)$_3$, H$_2$SO$_4$ cat., EtOH, b) Cl(O)P(OPh)$_2$, anhydrous pyridine, DMAP cat., c) H$_2$ 50 psi, crystalline PtO$_2$, EtOH, d) H$_2$O, 65° C., e) aqueous NaOH up to pH=7, f) Dowex H$^+$, 65° C.

The preparation of the dihydroxyacetonephosphate (DHAP) is a critical step of this synthesis. The chemical synthesis of dihydroxyacetonephosphate is carried out through five steps with overall yields about 60% (FIG. 3) according to Jung et al. disclosure (Jung, S. -H., Jeong, J. -H., Miller, P., Wong, C.-H., *J. Org. Chem.* 59 (1994) 7182).

Multienzyme systems for "in situ" generation of DHAP are an alternative approach. These are sophisticated processes demanding a very fine control of the reaction conditions and the presence of components in the reaction mixture which can hinder the isolation and purification of the final product (Fessner, W. D., Sinerius, G., *Angew. Chem. Int. Ed.* 33 (1994) 209; Charmantray, F., El Blidi, L., Gefflaut, T., Hecquet, L., Bolte, J., Lemaire, M., *J. Org. Chem.* 69 (2004) 9310, Sanchez-Moreno, I., Francisco Garcia-Garcia, J., Bastida, A., Garcia Junceda, E., *Chem. Commun.* (2004) 1634).

In the patent (US005329052A) and as it is disclosed by Von der Osten et al. (Von der Osten, C. H., Sinskey, A. J., Barbas, C. F., III, Pederson, R. L., Wang, Y. F., Wong, C. H., *J. Am. Chem. Soc.* 111 (1989) 3924), dihydroxyacetone is used in the presence of arsenic salts as a substitute of DHAP for enzymatic aldol addition. Although the process is simplified, the use of arsenic salts is not applicable due to their toxicity and, therefore, their environmental and health danger.

Already disclosed chemoenzymatic synthesis of iminocyclitols use about 8 steps from the acceptor aldehyde: two of them are enzymatic steps, the aldol addition of DHAP to the aldehyde, and the phosphate ester hydrolysis; and 6 chemical steps for DHAP synthesis, and the formation of the corresponding iminocyclitols. If the reaction is carried out with multienzyme systems, it requires two more enzymes: one for the formation of the key intermediate, DHAP, and another for regenerating the enzymatic phosphorilation reagent. Therefore, these are strategies with a lot of steps or very sophisticated and therefore with a limited industrial applicability.

SUMMARY OF THE INVENTION

An object of the invention is a chemoenzymatic process for the preparation of an iminocyclitol corresponding to formula (I), (II), (III) or (IV):

wherein:
$R^1$ and $R^2$ are the same or different, and independently selected from the group consisting of: H, OH, hydroxymethyl, methyl, ethyl, butyl, pentyl, hexyl, octyl, isopropyl, isobutyl, 2-methylbutyl, and benzyl;
$R^3$ is selected from the group consisting of: H, hydroxymethyl, hydroxyethyl, ethyl, butyl, pentyl, hexyl, octyl, dodecyl, isobutyl, isopropyl, isopentyl, 2-methylbutyl, benzyl, and phenylethyl;
n: 0 or 1;
the configurations of the carbon atoms to which $R^1$ and $R^2$ substituents are attached in the iminocyclitol of formula I are, the same or different, and independently selected from R and S; and the stereogenic centres (*) in the iminocyclitol of formula II, III or IV are, the same or different, and independently selected from R and S, characterized in that it comprises the following steps:
i) an aldol addition catalyzed by a D-fructose-6-phosphate aldolase enzyme (FSA), between the dihydroxyacetone (DHA) and an acceptor aminoaldehyde, the acceptor aminoaldehyde corresponding to formula V, VI or VII:

wherein
$R^1$, $R^2$, and n are as defined above;
the configurations of the carbon atoms to which $R^1$ and $R^2$ substituents are attached in formula V and the stereogenic centre of formulae VI and VII are the same or different, and independently selected from R and S; and
Cbz represents a benzyloxycarbonyl group;
and
ii) an intramolecular reductive amination of the addition adduct obtained in step (i) with $H_2$, in the presence of a metallic catalyst; optionally being carried out said step (ii) with an aldehyde of formula $R^3$—CHO, wherein $R^3$ is as defined above, resulting in a double reductive amination.

DETAILED DESCRIPTION OF THE INVENTION

The present inventors have found that it is possible to synthesize iminocyclitols by a process based on the use of the D-fructose-6-phosphate aldolase enzyme, hereinafter FSA, as a biological catalyst for the aldol addition reaction between dihydroxyacetone and an aminoaldehyde of formula V, VI or VII.

FSA ability for catalyzing the aldol addition between DHA and glycolaldehyde, D,L-glyceraldehyde-3-phosphate, D-glyceraldehyde and D-erythrose is known (Schürmann, M.; Sprenger, G. A. *J. Biol. Chem.* (2001) 276 11055). Furthermore, it is known that the active site of the FSA includes an arginine residue which is essential in order to satisfactorily arrange its natural substrate and give rise to the enzymatic reaction. The nature of the enzymatic active site determines the nature of compounds to be used as substrate and from Schurman et al., (supra) it can be concluded that the best acceptor substrates are the hydrophilic aldehydes described therein.

Surprisingly, the present inventors have found that although the aminoaldehydes of formula (V), (VI) and (VII) have quite different physico-chemical properties, being highly hydrophobic compared with the substrates known in the prior art, the aldol addition is carried out efficiently.

Furthermore, in Schürmann et al., (supra) the aldol addition adducts produced by FSA were not totally characterized by spectroscopic techniques nor the stereochemistry of the adducts was resolved. Therefore, it was not possible to deduce that the aminoaldehydes of formulae V, VI and VII were FSA substrates nor the final stereochemistry of the reaction was that suitable for the products of the present invention.

Additional advantages derived from the use of FSA are the following:

FSA uses dihydroxyacetone (DHA) for the aldol addition reaction instead dihydroxyacetone phosphate (DHAP), saving 5 synthetic steps with regard to DHAP-dependent aldolases methodology as described above, The step of the enzymatic hydrolysis of the phosphate group by acid phosphatase is avoided and, therefore, synthetic steps and production costs are diminished, FSA preparation and purification is simple and low cost, FSA is stable as a biocatalyst at 4° C. for at least seven months without losing activity, and It does not use nor generate toxic residues. As mentioned above, DHAP-aldolases can use DHA in the presence of arsenic salts, a high-toxicity product, harmful for the health and the environment.

Finally, another advantage of these biocatalysts is that they have some ability to control aldol addition stereochemistry. Thus, the configuration of the new generated stereogenic centres depends on the enzyme and not on the aldol addition reagents.

Therefore, an object of the invention is a chemoenzymatic process as defined above.

The elimination of the amine protecting group, and the intramolecular reductive amination in this stage (ii) may occur in one-pot reaction. Preferably, it occurs in a one-pot reaction.

A preferred embodiment is the process of the invention wherein the iminocyclitol is an iminocyclitol of formula I which is selected from the group consisting of: miglitol; miglustat; D-fagomine; 1-deoxynojirimycin; N-substituted derivatives thereof, such as N-butyl-D-fagomine; and 1,4-dideoxy-1,4-imino-D-arabinitol. Preferably, the iminocyclitol is selected from the group consisting of: D-fagomine; 1-deoxynojirimycin; N-butyl-D-fagomine; and 1,4-dideoxy-1,4-imino-D-arabinitol. More preferably, the iminocyclitol is selected from the group consisting of: D-fagomine; 1-deoxynojirimycin; and N-butyl-D-fagomine.

Another preferred embodiment of the invention is the process wherein the aminoaldehyde of (i) is a type V protected aminoaldehyde belonging, as an illustration and without limiting the scope of the invention, to the following group: N-Cbz-3-aminopropanal, and (S)—N-Cbz-3-amino-2-hydroxypropanal A particular embodiment of the invention is the process of the invention wherein the FSA enzyme used in step (i) corresponds to *E. Coli* FSA with SEQ ID NO2. D-fructose-6-phosphate aldolase (FSA) enzyme used in the present invention has been cloned in *E. coli* MC4100 strain, derived from *E. coli* K-12 strain (Schürmann, M.; Sprenger, G. A. *J. Biol. Chem.* (2001) 276 11055; Casadaban, M. J. (1976) *J. Mol. Biol.* 104, 541-555) and subsequently purified. Thus, the preferred FSA enzyme used consists in the wild type which naturally occurs in said microorganism and with an aminoacid sequence corresponding to SEQ ID NO2. Any other wild type D-fructose-6-phosphate aldolase (FSA) enzyme can be isolated and identified in other microorganisms due to the information and processes existing in the state of the art. Therefore, other embodiment of the present invention is the process wherein the FSA enzyme is an enzyme with an analogous sequence to SEQ ID NO2, isolated from a microorganism other than *E. coli*.

Figure 4:
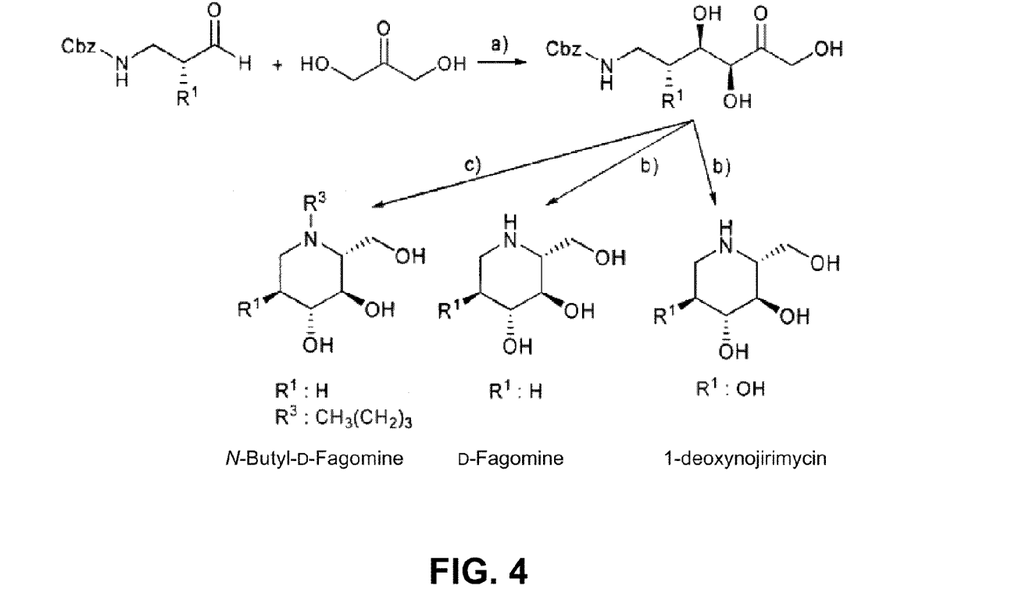
FIG. 4. Scheme of the exemplified reactions of the use of the process of the invention for the synthesis of D-fagomine, N-butyl-D-fagomine, and 1-deoxynojirimycin: a) FSA, b) Pd/C H$_2$ pressure 50 psi, and c) CH$_3$CH$_2$CH$_2$COH, Pd/C H$_2$ pressure 50 psi.

As used herein, the term "analogous" intends to include any aminoacid sequence which can be isolated from a microorganism and have the aldol addition ability between the dihydroxyacetone (DHA) and an acceptor aldehyde of formula V, VI, or VII (FIG. 4). Generally, an analogous aminoacid sequence is substantially homologous to the previously cited aminoacid sequence. As used herein, the expression "substantially homologous" means that the aminoacid sequences in question have an identity degree of at least 30%, preferably of at least 85%, or more preferably of at least 95%.

Other particular object of the invention is the process of the invention wherein the metallic catalyst used in step (ii) belongs, as an illustration and without limiting the scope of the invention, to the following group: Pd, Pt, Rh, and combinations of Pd and sodium cyanoborohydride (NaCNBH$_3$).

EXAMPLES

Next, five examples illustrate the use of this process for the preparation of D-fagomine, N-butyl-D-fagomine, 1-deoxynojirimycin, and 1,4-dideoxy-1,4-imino-D-arabinitol (DAB). The general scheme of the reactions detailed next is shown on FIG. 4.

Example 1

D-Fagomine Synthesis

Step 1) Preparation of the Aldol Addition Adduct.

Starting aldehyde, N-Cbz-3-aminopropanal, was obtained from 3-aminopropanol by conventional processes disclosed by Espelt et al. (Espelt, L., Parella, T., Bujons, J., Solans, C., Joglar, J., Delgado, A., Clapés, P., *Chem. -Eur. J.* 9 (2003) 4887; Ocejo, M., Vicario, J. L., Badia, D., Carrillo, L., Reyes, E., *Synlett* (2005) 2110).

N-Cbz-3-aminopropanal (2.1 g, 22.9 mmol) was dissolved with dimethylformamide (40 mL) in a reactor of 250 mL of volume and equipped with orbital stirring. Dihydroxyacetone (4.7 g, 22.9 mmol) and FSA enzyme in raw powder (2.09 g, 3445 U) were added to this solution dissolved with boric borate buffer 50 mM pH 7 (155 mL). The mixture was left to react under orbital stirring (120 rpm) at 4° C. for 24 hours. The reaction conversion at this point was greater than 98%. Next, MeOH (200 mL) was added to the reaction mixture, appearing a precipitate which was separated by centrifugation. The supernatant was purified by reverse phase liquid chromatography. Pure fractions were pooled, the solvent was evaporated obtaining 4.7 g of a white solid (yield 69%, diastereomeric excess 99%).

The preparation and purification of FSA were carried out from crude protein extract from the fermentation and cell disruption by thermal treatment at 75° C. for 40 minutes (Schurmann, M., Sprenger, G. A, *J. Biol. Chem.* 276 (2001) 11055; Thorell, S., Schurmann, M., Sprenger, G. A, Schneider, G., *J. Mol. Biol.* 319 (2002) 161; Schurmann, M., Sprenger, G. A., *J. Mol. Catal. B-Enzym.* 19 (2002) 247). The protein extract was obtained from *E. coli* MC4100 strain, derived from *E. coli* K-12 strain (Casadaban, M. J. *J. Mol. Biol.* (1976) 104, 541), which comprises the coding sequence of *E. coli* FSA protein (SEQ ID NO1). Cloning, ligation to a plasmid, and transformation into an *E. coli* strain are described in detail in Schurmann, M., Sprenger, G. A., *J. Biol. Chem.* 276 (2001) 11055; The FSA protein thus obtained (SEQ ID NO2) retains its activity while protein impurities precipitate, being separated by simple filtration or centrifugation.

Step 2) Deprotection and Intramolecular Reductive Amination.

The adduct obtained in the last step (373 mg, 1.26 mmol) was dissolved in ethanol/water 1:9 (50 mL). The solution was kept under $H_2$ atmosphere at 50 psi of pressure in the presence of palladium over carbon (100 mg). At these conditions, the elimination of Cbz group and the intramolecular reductive amination proceeded simultaneously for 12 hours. Alternatively, the adduct obtained in the last step (373 mg, 1,26 mmol) was dissolved in ethanol/water 1:9 (50 mL) in the presence of sodium cyanoborohydride ($NaCNBH_3$) (50 mg). The solution was kept under $H_2$ atmosphere at room pressure in the presence of palladium over carbon (100 mg). At these conditions, the elimination of the Cbz group was carried out by the palladium action and the intramolecular reductive amination by the presence of $NaCNBH_3$. Both reactions proceed simultaneously for 6 hours. Next, the reaction mixture was filtered over deactivated alumina and the filtrate was evaporated obtaining 164 mg of D-fagomine solid (yield 89%).

$[\alpha]_D^{22}$+20.4 (c 1.0 in $H_2O$); $\delta_H$ (500 MHz; $D_2O$; 22° C.) 3.86 (1H, dd, J 11.8 and 3.0, 7-H), 3.66 (1H, dd, J 11.8 and 6.5, 7-H), 3.56 (1H, ddd, J 11.5, 9.0 and 5.0, 4-H), 3.21 (1H t, J 9.5 and 9.5, 3-H), 3.06 (1H, ddd, J 12.9, 4.4 and 2.3, 6-H), 2.68 (1H, dt, J 12.94, 12.92 and 2.70, 6-H), 2.61 (1H, ddd, J 9.68, 6.44 and 2.97, 2-H), 2.01 (1H, tdd, J 13.0, 4.9, 2.5 and 2.5, 5-H) y 1.48 ppm (1H, dq, J 13.0, 12.9, 11.5 and 4.5, 5-H); $\delta_c$ (101 MHz; $D_2O$; 22° C.) 72.9, 72.7, 61.1, 60.9, 42.6 and 32.1.

Example 2

N-Butyl-D-Fagomine Synthesis

Step 1) Preparation of the Aldol Addition Adduct as in the Previous Section.

Step 2) Deprotection and Double Reductive Amination.

The adduct resulting from the previous step (150 mg, 0.51 mmol) and butanal were dissolved in ethanol/water 7:3 (10 mL). Palladium over carbon (50 mg) was added to this solution and the mixture was left to react under $H_2$ at 50 psi for 12 hours. Next, the process was similar to that of the previous example, and 52 mg of N-butyl-D-fagomine solid were obtained (yield 52%) after the purification of the reaction crude by a silica column using $MeOH/CHCl_3$ mixtures as eluents.

$[\alpha]_D^{22}$=−24.5 (c 1.2 in MeOH); $\delta H$ (500 MHz, $D_2O$, 22° C.) 3.90 (1H, dd, J 12.7, and 2.4, 7-H), 3.82 (1H, dd, J 12.7 and 2.9, 7-H), 3.45 (1H, ddd, J 11.5, 9.1 and 5.1, 4-H), 3.30 (1H, t, J 9.4, 3-H), 2.90 (1H, td, J 12.2, 3.5 and 3.5, 6-H), 2.73 (1H, ddd, J 13.3, 11.2 y 5.4, 8-H), 2.50 (1H, ddd, J 13.3, 11.1 and 5.2, 8-H), 2.36 (1H, dt, J 12.6, 12.6 and 2.4, 6-H), 2.16 (1H, td, J 9.8, 2.6 and 2.6 Hz, 2-H), 1.92 (1H tdd, J 12.7, 5.0, 2.5 and 2.5, 5-H), 1.55-1.35 (3H, m, 5-H and 2×9-H), 1.30-1.21 (2H, m, 2×10-H) and 0.88 (3H, t, J 7.4 and 7.4, 11-Me); $\delta_c$, (101 MHz, $D_2O$, 22° C.) 73.2, 72.0, 65.8, 58.1, 52.2, 49.1, 30.5, 25.6, 20.4 and 13.3.

Example 3

1-deoxynojirimycin Synthesis

Step 1) Preparation of the Aldol Addition Adduct.

Starting aldehyde, (S)-N-Cbz-3-amino-2-hydroxypropanal, was obtained from (S)-3-amino-2-hydroxypropanol by a process disclosed by De Luca et al. (De Luca, L., Giacomelli, G., Porcheddu, A., *Org. Lett.* 3 (2001) 3041). The process was equivalent to that disclosed in Example 1, but in this case with the difference of performing the reaction at 25° C.

Step 2) Deprotection and Intramolecular Reductive Amination.

It was performed as in Example 1 obtaining 164 mg (yield 89%) of a white solid of 1-deoxynojirimycin. $[\alpha]_D^{22}$+48.0 (C 1.0 at $H_2O$). $^1H$ NMR (500 MHz, $D_2O$. $\delta$ ppm 3.74 (dd, J=11.8, 3.00 Hz, 1H), 3.56 (dd, J=11.9, 6.2 Hz, 1H), 3.4 (ddd, J=10.96, 9.06, 5.25 Hz, 1H), 3.24 (t, J=9.1, 9.1 Hz, 1H), 3.18 (t, J=9.4, 9.4 Hz, 1H), 3.1 (dd, J=12.3, 5.2 Hz, 1H), 2.54 (hept, J=9.4, 6.0, 3.0, 1H), 2.43 (dd, J=12.3, 11.0 Hz, 1H).

Example 4

Synthesis of 1-deoxynojirimycin

Step 1) Preparation of the adduct from aldolic addition.

The starting aldehyde, (R,S)-N-Cbz-3-amino-2-hydroxy-propanal, was obtained from (R,S)-N-Cbz-3-amino-2-hydroxy-propanol (1 g, 4.4 mmol) by oxidation with IBX (o-iodoxybenzoic acid). In a 250 mL reactor equipped with orbital shaking and reflux N-Cbz-3-amino-2-hydroxy-propanol (1 g, 4.4 mmol) was dissolved in ethyl acetate (150 mL). To this solution IBX (2,5 g; 2 equivalents) was added and the reaction was kept under reflux for 3 h.

The resulting solution was filtered and the ethyl acetate layer washed with 5% (p/v) $NaHCO_3$ and saturated NaCl to eliminate reaction by-products. The ethyl acetate solution which contained (R,S)—N-Cbz-3-amino-2-hydroxy-propanal, was added over an aqueous solution of dihydroxyacetone (510 mg, 5.7 mmol) and crude powder FSA (235 mg, 3445 U) in boric-borate buffer 50 mM pH 8 (250 mL) in a 500 mL reactor. The ethyl acetate was evaporated from the resulting two-phase mixture and this allowed the diffusion of the aldehyde into the aqueous phase. The reaction was then kept under orbital shaking (120 rpm) for 24 hours at 25° C. At this point the reaction conversion was higher than 98%. Then, MeOH (250 mL) was added to the crude reaction mixture and a solid residue was separated by centrifugation. The supernatant was purified by reversed-phase liquid chromatography to obtain a white solid (600 mg, 44% yield).

Step 2) Deprotection and Intramolecular Reductive Amination.

The adduct obtained in the previous step (600 mg, 1.91 mmol) was dissolved in ethanol/water 1:4 (80 mL). The solution was kept for 12 h under $H_2$ atmosphere at a pressure of 50 psi in the presence of palladium/charcoal (176 mg). Under these conditions both the elimination of Cbz and the intramolecular reductive amination proceeded simultaneously over a period of 12 hours. Then the crude reaction mixture was filtered over neutral alumina and the filtrate evaporated to obtain a white solid (164 mg, 89% yield).

$^1$H NMR (500 MHz, $D_2O$) δ ppm 3.74 (dd, J=11.8, 3.00 Hz, 1H), 3.56 (dd, J=11.9, 6.2 Hz, 1H), 3.4 (ddd, J=10.96, 9.06, 5.25 Hz, 1H), 3.24 (t, J=9.1, 9.1 Hz, 1H), 3.18 (t, J=9.4, 9.4 Hz, 1H), 3.1 (dd, J=12.3, 5.2 Hz, 1H), 2.54 (hept, J=9.4, 6.0, 3.0, 1H), 2.43 (dd, J=12.3, 11.0 Hz, 1H).

Example 5

Synthesis of 1,4-dideoxy-1,4-imino-D-arabinitol (DAB)

Step 1) Preparation of an Adduct from Aldolic Addition.

The starting aldehyde N-Cbz-2-aminoetanal was obtained from 2-aminoetanol by standard procedures such as those described by Espelt, L., Parella, T., Bujons, J., Solans, C., Joglar, J., Delgado, A., Clapés, P., *Chem.-Eur. J.* 9 (2003) 4887; Ocejo, M., Vicario, J. L., Badia, D., Carrillo, L., Reyes, E., *Synlett* (2005)2110.

In a 250 mL reactor equipped with orbital shaking N-Cbz-3-aminoetanal (1.51 g, 7.8 mmol) was dissolved in dimethylformamide (8 mL). To this solution dihydroxyacetone (0,71 g, 7.9 mmol) and a lyophilized preparation with FSA activity (0.7 g, 1150 U) dissolved in boric-borate buffer 50 mM pH 7.0 (72 mL) were added. The reaction proceeded under orbital shaking (120 rpm) for 120 hours at 25° C. At this point the reaction conversion was 49%. Then MeOH (100 mL) was added and a solid residue was separated by centrifugation. The supernatant was purified by reversed-phase liquid chromatography. The pure fractions were collected and the solvent evaporated to obtain a white solid (0.50 g, 23% yield)

Step 2) Deprotection and Intramolecular Reductive Amination.

The adduct obtained in the previous step (500 mg, 1.77 mmol) was dissolved in ethanol/water 1:9 (90 mL). The solution was kept for 12 h under $H_2$ atmosphere at a pressure of 50 psi in the presence of Pd/C (204 mg) as catalyst. Then the crude reaction mixture was filtered over neutral alumina and the filtrate evaporated to obtain a white solid (253 mg). The final product was purified from this solid by cation exchange chromatography to obtain a 10 mM aqueous $NH_3$ solution. The pure fractions were pooled and the solvent evaporated to obtain a white solid (129 mg, 10% global yield, 99% diastereomeric excess).

$[\alpha]_D^{20}$+26.2 (c 1.0 en $H_2O$); $[\alpha]_D^{20}$+35.2 (c 1.0 en MeOH)
$^1$H NMR (500 MHz, $D_2O$, 22° C.) δ (ppm): 4.35 (m, 1H, H4), 4.11 (t, J=3.3 Hz, 1H, H3), 3.97 (dd, J=12.2, 4.6 Hz, 1H, H6), 3.85 (dd, J=12.2, 8.3 Hz, 1H, 6H), 3.63 (dd, J=8.3, 4.2 Hz, 1H, H2), 3.59 (dd, J=12.6, 4.8 Hz, 1H, H 5), 3.37 (dd, J=12.6, 2.7 Hz, 1H, H5). $^{13}$C NMR (101 MHz, $D_2O$, 22° C.) δ (ppm): 78.37 (C3), 77.00 (C4), 69.30 (C2), 61.66 (C6), 52.68 (C5)

The invention claimed is:

1. Chemoenzymatic process for the preparation of an iminocyclitol of formula (I), (II), (III) or (IV):

(I)

(II)

(III)

(IV)

wherein:
- $R^1$ and $R^2$ are the same or different, and independently selected from the group consisting of: H, OH, hydroxymethyl, methyl, ethyl, butyl, pentyl, hexyl, octyl, isopropyl, isobutyl, 2-methylbutyl, and benzyl;
- $R^3$ is selected from the group consisting of: H, hydroxymethyl, hydroxyethyl, ethyl, butyl, pentyl, hexyl, octyl, dodecyl, isobutyl, isopropyl, isopentyl, 2-methylbutyl, benzyl, and phenylethyl;
- n: 0 or 1;
- the configurations of the carbon atoms to which $R^1$ and $R^2$ substituents are attached in the iminocyclitol of formula I are, the same or different, and independently selected from R and S; and
- the stereogenic centres * in the iminocyclitol of formula II, III or IV are, the same or different, and independently selected from R and S;

the process comprising:
i) an aldol addition catalyzed by a D-fructose-6-phosphate aldolase enzyme (FSA), wherein the FSA enzyme has an identity degree with the amino acid sequence of SEQ ID NO: 2 of at least 85%, between the dihydroxyacetone (DHA) and an acceptor aminoaldehyde, the aminoaldehyde corresponding to formula V, VI or VII:

(V)

(VI)

(VII)

wherein
$R^1$, $R^2$ and n are as defined above;
the configurations of the carbon atoms to which $R^1$ and $R^2$ substituents are attached in formula V and the stereogenic centre of formulae VI and VII are the same or different, and independently selected from R and S; and
Cbz represents a benzyloxycarbonyl group; and
ii) an intramolecular reductive amination of the addition adduct obtained in step (i) with $H_2$, in the presence of a metallic catalyst, optionally being carried out said step (ii) with an aldehyde of formula $R^3$—CHO, wherein $R^3$ is as defined above, resulting in a double reductive amination.

2. The process according to claim 1, wherein the iminocyclitol is selected from the group consisting of: miglitol; miglustat; D-fagomine; 1-deoxynojirimycin; N-butyl-D-fagomine; and 1,4-dideoxy-1,4-imino-D-arabinitol.

3. The process according to claim 2, wherein the iminocyclitol is selected from the group consisting of: D-fagomine; 1-deoxynojirimycin; N-butyl-D-fagomine; and 1,4-dideoxy-1,4-imino-D-arabinitol.

4. The process according to claim 3, wherein the iminocyclitol is selected from the group consisting of: D-fagomine, 1-deoxynojirimycin, and N-butyl-D-fagomine.

5. Process according to claim 1, wherein the aminoaldehyde in (i) is a type V protected aminoaldehyde selected from the group consisting of:
N-Cbz-3-aminopropanal, and (S)-N-Cbz-3-amino-2-hydroxypropanal.

6. The process according to claim 1, wherein the metallic catalyst used in step (ii) is selected from the group consisting of: Pd, Pt, Rh, and combinations of Pd with sodium cyanoborohydride ($NaCNBH_3$).

7. The process according to claim 1, wherein the FSA enzyme has an identity degree with the amino acid sequence of SEQ ID NO: 2 of at least 95%.

8. The process according to claim 7, wherein the FSA enzyme consists of the amino acid sequence of SEQ ID NO2.

* * * * *

SEQUENCE LISTING

<160> NUMBER OF SEQ ID NOS: 2

<210> SEQ ID NO 1
<211> LENGTH: 663
<212> TYPE: DNA
<213> ORGANISM: Escherichia coli
<220> FEATURE:
<221> NAME/KEY: CDS
<222> LOCATION: (1)..(663)

<400> SEQUENCE: 1

```
atg gaa ctg tat ctg gat act tca gac gtt gtt gcg gtg aag gcg ctg      48
Met Glu Leu Tyr Leu Asp Thr Ser Asp Val Val Ala Val Lys Ala Leu
1               5                   10                  15 tca cgt att ttt ccg ctg gcg ggt gtg acc act aac cca agc att atc      96
Ser Arg Ile Phe Pro Leu Ala Gly Val Thr Thr Asn Pro Ser Ile Ile
            20                  25                  30 gcc gcg ggt aaa aaa ccg ctg gat gtt gtg ctt ccg caa ctt cat gaa     144
Ala Ala Gly Lys Lys Pro Leu Asp Val Val Leu Pro Gln Leu His Glu
        35                  40                  45 gcg atg ggc ggt cag ggg cgt ctg ttt gcc cag gta atg gct acc act     192
Ala Met Gly Gly Gln Gly Arg Leu Phe Ala Gln Val Met Ala Thr Thr
    50                  55                  60 gcc gaa ggg atg gtt aat gac gcg ctt aag ctg cgt tct att att gcg     240
Ala Glu Gly Met Val Asn Asp Ala Leu Lys Leu Arg Ser Ile Ile Ala
65                  70                  75                  80 gat atc gtg gtg aaa gtt ccg gtg acc gcc gag ggg ctg gca gct att     288
Asp Ile Val Val Lys Val Pro Val Thr Ala Glu Gly Leu Ala Ala Ile
                85                  90                  95
```

-continued

```
aag atg tta aaa gcg gaa ggg att ccg acg ctg gga acc gcg gta tat    336
Lys Met Leu Lys Ala Glu Gly Ile Pro Thr Leu Gly Thr Ala Val Tyr
        100                 105                 110 ggc gca gca caa ggg ctg ctg tcg gcg ctg gca ggt gcg gaa tat gtt    384
Gly Ala Ala Gln Gly Leu Leu Ser Ala Leu Ala Gly Ala Glu Tyr Val
    115                 120                 125 gcg cct tac gtt aat cgt att gat gct cag ggc ggt agc ggc att cag    432
Ala Pro Tyr Val Asn Arg Ile Asp Ala Gln Gly Gly Ser Gly Ile Gln
130                 135                 140 act gtg acc gac tta cac cag tta ttg aaa atg cat gcg ccg cag gcg    480
Thr Val Thr Asp Leu His Gln Leu Leu Lys Met His Ala Pro Gln Ala
145                 150                 155                 160 aaa gtg ctg gca gcg agt ttc aaa acc ccg cgt cag gcg ctg gac tgc    528
Lys Val Leu Ala Ala Ser Phe Lys Thr Pro Arg Gln Ala Leu Asp Cys
                165                 170                 175 tta ctg gca gga tgt gaa tca att act ctg cca ctg gat gtg gca caa    576
Leu Leu Ala Gly Cys Glu Ser Ile Thr Leu Pro Leu Asp Val Ala Gln
            180                 185                 190 cag atg att agc tat ccg gcg gtt gat gcc gct gtg gcg aag ttt gag    624
Gln Met Ile Ser Tyr Pro Ala Val Asp Ala Ala Val Ala Lys Phe Glu
        195                 200                 205 cag gac tgg cag gga gcg ttt ggc aga acg tcg att taa                663
Gln Asp Trp Gln Gly Ala Phe Gly Arg Thr Ser Ile
    210                 215                 220
```

<210> SEQ ID NO 2
<211> LENGTH: 220
<212> TYPE: PRT
<213> ORGANISM: Escherichia coli

<400> SEQUENCE: 2

```
Met Glu Leu Tyr Leu Asp Thr Ser Asp Val Val Ala Val Lys Ala Leu
1               5                   10                  15

Ser Arg Ile Phe Pro Leu Ala Gly Val Thr Thr Asn Pro Ser Ile Ile
            20                  25                  30

Ala Ala Gly Lys Lys Pro Leu Asp Val Val Leu Pro Gln Leu His Glu
        35                  40                  45

Ala Met Gly Gly Gln Gly Arg Leu Phe Ala Gln Val Met Ala Thr Thr
    50                  55                  60

Ala Glu Gly Met Val Asn Asp Ala Leu Lys Leu Arg Ser Ile Ile Ala
65                  70                  75                  80

Asp Ile Val Val Lys Val Pro Val Thr Ala Glu Gly Leu Ala Ala Ile
                85                  90                  95

Lys Met Leu Lys Ala Glu Gly Ile Pro Thr Leu Gly Thr Ala Val Tyr
            100                 105                 110

Gly Ala Ala Gln Gly Leu Leu Ser Ala Leu Ala Gly Ala Glu Tyr Val
        115                 120                 125

Ala Pro Tyr Val Asn Arg Ile Asp Ala Gln Gly Gly Ser Gly Ile Gln
    130                 135                 140

Thr Val Thr Asp Leu His Gln Leu Leu Lys Met His Ala Pro Gln Ala
145                 150                 155                 160

Lys Val Leu Ala Ala Ser Phe Lys Thr Pro Arg Gln Ala Leu Asp Cys
                165                 170                 175

Leu Leu Ala Gly Cys Glu Ser Ile Thr Leu Pro Leu Asp Val Ala Gln
            180                 185                 190
```

```
Gln Met Ile Ser Tyr Pro Ala Val Asp Ala Ala Val Ala Lys Phe Glu
        195             200                 205
Gln Asp Trp Gln Gly Ala Phe Gly Arg Thr Ser Ile
    210             215             220
```